(12) United States Patent
Bingel et al.

(10) Patent No.: US 6,444,606 B1
(45) Date of Patent: Sep. 3, 2002

(54) SUPPORTED CATALYST SYSTEM, METHOD FOR THE PRODUCTION AND USE THEREOF IN OLEFIN POLYMERIZATION

(75) Inventors: Carsten Bingel, Kriftel; Markus Goeres, Eschborn; Volker Fraaije, Frankfurt; Andreas Winter, Glashütten, all of (DE)

(73) Assignee: Basell Polypropylen GmbH, Ludwigshafen (DE)

( * ) Notice: Subject to any disclaimer, the term of this patent is extended or adjusted under 35 U.S.C. 154(b) by 0 days.

(21) Appl. No.: 09/242,168

(22) PCT Filed: Mar. 5, 1998

(86) PCT No.: PCT/EP98/01233

§ 371 (c)(1),
(2), (4) Date: Feb. 10, 1999

(87) PCT Pub. No.: WO98/40416

PCT Pub. Date: Sep. 17, 1998

(30) Foreign Application Priority Data

| Mar. 7, 1997 | (DE) | 197 09 402 |
| Apr. 2, 1997 | (DE) | 197 13 546 |
| Dec. 23, 1997 | (DE) | 197 57 563 |

(51) Int. Cl.$^7$ .............................. C08F 4/44; C08F 4/16; B01J 31/38
(52) U.S. Cl. ................. 502/152; 502/104; 502/117; 526/160; 526/943; 526/352; 526/127
(58) Field of Search ................. 526/160, 943, 526/352; 502/104, 162

(56) References Cited

U.S. PATENT DOCUMENTS

| 5,240,894 A | 8/1993 | Burkhardt et al. | 502/108 |
| 5,416,178 A | 5/1995 | Winter et al. | 526/160 |
| 5,661,096 A | 8/1997 | Winter et al. | 502/103 |
| 5,770,753 A | 6/1998 | Kueber et al. | 556/11 |
| 5,859,272 A * | 1/1999 | Imuta et al. | 556/11 |

FOREIGN PATENT DOCUMENTS

| EP | 302424 | 2/1989 |
| EP | 576970 | 1/1994 |
| EP | 589638 | 3/1994 |
| EP | 697419 | 2/1996 |
| EP | 704461 | 4/1996 |
| WO | WO 94/28034 | * 12/1994 |
| WO | 95/12622 | 5/1995 |
| WO | 96/35729 | 11/1996 |
| WO | 97/11775 | 4/1997 |

OTHER PUBLICATIONS

Wild et al., *J. Org. Chem.*, 288 (1985) 63–67.
Harlan et al., *J. Am. Chem. Soc.*, 117 (1995) 6465–6474.
Harlan et al., *Organometallics*, 13 (1994), 2957–2969.
Pasynkiewicz, *Polyhedron*, vol. 9, No. 2, pp. 429–453.
Zambelli et al., *Macromolecules*, vol. 8, No. 5, Sep.–Oct. 1975.
Cheng, *Makromol. Chem.*, 190 (1989), 1931–43.
Tsutsui et al., *Polymer*, vol. 30, Jul. 1989, pp. 1350–1356.
Randall, Polymer Sequence Determination: Carbon 13 NMR Method, Acad. Press, 1978, pp. 23–40.

* cited by examiner

Primary Examiner—David W. Wu
Assistant Examiner—R. Harlan
(74) Attorney, Agent, or Firm—Keil & Weinkauf

(57) ABSTRACT

The invention relates to a catalyst system obtained by mixing at least one metallocene, at least one co-catalyst and at least one support which is rendered inert. The invention further relates to a method for producing a free flowing supported catalyst system wherein a) a metallocene/co-catalyst mixture is produced in a solvent or suspension agent, b) the metallocene/co-catalyst mixture is applied to a porous preferably inorganic dehydrated support, c) the solvent is removed from the resulting mixture, d) the supported catalyst system is isolated. The present invention also relates to homopolymers and/or copolymers having the preferred formula $R_m$—CH=CH—$R_n$ for the monomer, wherein $R_m$ and $R_n$ are the same or different and mean a hydrogen atom or a group containing carbon with 1 to 10 C atoms, and $R_m$ and $R_n$ can form one or several rings with the binding atoms, which can be obtained with a catalyst system. Finally, the invention relates to the use of the inventive polymers from producing tear-resistant, hard and stiff shaped bodies such as fibers, filaments, injection-molded parts, films, plates or large hollow bodies such as tubes.

11 Claims, No Drawings

SUPPORTED CATALYST SYSTEM, METHOD FOR THE PRODUCTION AND USE THEREOF IN OLEFIN POLYMERIZATION

The present invention relates to substituted metallocenes and highly active supported catalyst systems which can advantageously be used in olefin polymerization, and to a process for their preparation and also to polymers which are prepared using the supported catalyst systems.

Processes for preparing polyolefins using soluble, homogeneous catalyst systems comprising a transition metal component of the metallocene type and a cocatalyst component of the type of an aluminoxane, a Lewis acid or an ionic compound are known. These catalysts have a high activity and give polymers and copolymers having a narrow molar mass distribution.

In polymerizations using soluble, homogeneous catalyst systems, heavy deposits are formed on reactor walls and the stirrer if the polymer is obtained as a solid. These deposits are formed by agglomeration of the polymer particles whenever metallocene and/or cocatalyst are present in dissolved form in the suspension. The deposits in the reactor systems quickly reach considerable thicknesses and have a high strength. They prevent heat exchange to the cooling medium and therefore have to be removed regularly. Such homogeneous catalyst systems cannot be used industrially in the liquid monomer or in the gas phase.

To avoid deposit formation in the reactor, supported catalyst systems in which the metallocene and/or the aluminum compound serving as cocatalyst is/are fixed on an inorganic support material have been proposed.

EP-A-0 576 970 discloses metallocenes and corresponding supported catalyst systems.

At industrially relevant polymerization temperatures of from 50° C. to 80° C., the supported catalyst systems give polymers, in particular polypropylenes, having melting points of at most 156° C. Typical values for such systems are merely in the region of 150° C. For many polymer applications, for example extrusion and injection molding, such products are not satisfactory in respect of hardness and mechanical strength.

It is an object of the present invention to provide supported etallocene catalysts which, owing to their high regiospecificity and stereospecificity, give polymers having a higher melting point under industrially relevant polymerization conditions and provide an environmentally friendly and economical process for preparing the polymers.

We have found that this object is achieved by a supported catalyst system comprising at least one specifically substituted metallocene, at least one cocatalyst, at least one passivated support and, if desired, at least one further additive component. According to the present invention, the catalyst system is prepared by mixing at least one specifically substituted metallocene, at least one cocatalyst and at least one passivated support.

As metallocene component of the catalyst system of the present invention, use is made of at least one compound of the formula I below,

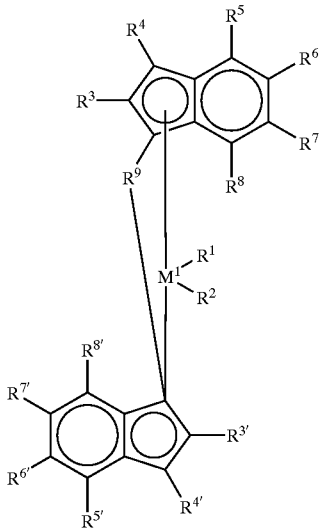

(I)

where $M^1$ is metal of group IVb of the Periodic Table of the Elements, $R^1$ and $R^2$ are identical or different and are each a hydrogen atom, a $C_1$–$C_{10}$-alkyl group, a $C_1$–$C_{10}$-alkoxy group, a $C_6$–$C_{20}$-aryl group, a $C_6$–$C_{10}$-aryloxy group, a $C_2$–$C_{10}$-alkenyl group, an OH group, an $NR^{12}_2$ group, where $R^{12}$ is a $C_1$–$C_{10}$-alkyl group or $C_6$–$C_{14}$-aryl group, or a halogen atom, $R^3$, $R^4$, $R^6$, $R^7$, $R^8$ and also $R^{3'}$, $R^{4'}$, $R^{6'}$, $R^{7'}$ and $R^{8'}$ are identical or different and are each a hydrogen atom, a hydrocarbon group which may be halogenated, linear, cyclic or branched, for example a $C_1$–$C_{10}$-alkyl group, $C_2$–$C_{10}$-alkenyl group, $C_6$–$C_{20}$-aryl group, a $C_7$–$C_{40}$-arylalkyl group, a $C_7$–$C_{40}$-alkylaryl group or a $C_8$–$C_{40}$-arylalkenyl group, with the proviso that $R^3$ and $R^{3'}$ are not hydrogen, and $R^5$ and $R^{5'}$ are identical or different and are each a $C_6$–$C_{40}$-aryl group which in the para position to the bonding position on the indenyl ring bears a substituent $R^{13}$

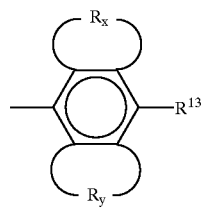

where x, y=0, 1 and x+y=0, 1 or 2, where the aromatic ring system x and/or the aromatic ring system y can also be linked to the radicals $R^6$, $R^{6'}$, or $R^4$, $R^{4'}$, and $R^{13}$ is a $C_2$–$C_{20}$-alkyl radical, a $C_2$–$C_{20}$-alkenyl radical, a $C_6$–$C_{24}$-aryl radical, a $C_7$–$C_{40}$-arylalkyl radical, a $C_7$–$C_{40}$-alkylaryl radical, a $C_8$–$C_{40}$-arylalkenyl radical, where the hydrocarbon radicals may also be halogenated or partially halogenated by fluorine, chlorine or bromine, —$NR^{14}_2$, —$PR^{14}_2$, —$SR^{14}$, —$OR^{14}$, —$SiR_3^{14}$, —$NR_3^{14}$ or —$PR_3^{14}$, where $R^{14}$ is as defined for $R^3$, $R^9$ is a bridge $$—O—\underset{\underset{R^{11}}{|}}{\overset{\overset{R^{10}}{|}}{M^2}}—O—, \quad —\underset{\underset{R^{11}}{|}}{\overset{\overset{R^{10}}{|}}{C}}—, \quad —O—\underset{\underset{R^{11}}{|}}{\overset{\overset{R^{10}}{|}}{M^2}}—,$$

$$—\underset{\underset{R^{11}}{|}}{\overset{\overset{R^{10}}{|}}{C}}—\underset{\underset{R^{11}}{|}}{\overset{\overset{R^{10}}{|}}{M^2}}—, \quad —\underset{\underset{R^{11}}{|}}{\overset{\overset{R^{10}}{|}}{M^2}}—, \quad —\underset{\underset{R^{11}}{|}}{\overset{\overset{R^{10}}{|}}{M^2}}—\underset{\underset{R^{11}}{|}}{\overset{\overset{R^{10}}{|}}{M^2}}—, \quad —\underset{\underset{R^{11}}{|}}{\overset{\overset{R^{10}}{|}}{C}}—\underset{\underset{R^{11}}{|}}{\overset{\overset{R^{10}}{|}}{C}}—,$$

$$—\underset{\underset{R^{11}}{|}}{\overset{\overset{R^{10}}{|}}{M^2}}—[\underset{\underset{R^{11}}{|}}{\overset{\overset{R^{10}}{|}}{C}}]_x—\underset{\underset{R^{11}}{|}}{\overset{\overset{R^{10}}{|}}{M^2}}—, \quad —\underset{\underset{R^{11}}{|}}{\overset{\overset{R^{10}}{|}}{C}}—\underset{\underset{R^{11}}{|}}{\overset{\overset{R^{10}}{|}}{C}}—\underset{\underset{R^{11}}{|}}{\overset{\overset{R^{10}}{|}}{C}}—,$$

$>BR^{10}, \quad >AlR^{10}, \quad —Ga—, \quad —O—, \quad —S—,$ $>SO, \quad >SO_2, \quad >NR^{10}, \quad >OO, \quad >PR^{10},$ or $>R(O)R^{10}$, where $R^{10}$ and $R^{11}$, even when bearing the same index, can be identical or different and are each a hydrogen atom, a halogen atom or a $C_1$–$C_{40}$-group such as a $C_1$–$C_{20}$-alkyl group, a $C_1$–$C_{10}$-fluoroalkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group or $R^{10}$ and $R^{11}$ together with the atoms connecting them form one or more rings, z is an integer from zero to 18 and $M^2$ is silicon, germanium or tin, and $R^9$ may also link two units of the formula I to one another.

The 4,5,6,7-tetrahydroindenyl analogues corresponding to the compounds I are likewise of importance.

In formula I, it is preferred that

M1 is zirconium, hafnium or titanium, $R^1$ and $R^2$ are identical and are methyl or chlorine, $R^3$ and $R^{3'}$, are identical or different and are each a hydrocarbon group which may be halogenated, linear, cyclic or branched, for example a $C_1$–$C_{10}$-alkyl group, $C_2$–$C_{10}$-alkenyl group or a $C_7$–$C_{40}$-alkylaryl group, $R^9$ is $R^{10}R^{11}Si=$, $R^{10}R^{11}Ge=$, $R^{10}R^{11}C=$ or —($R^{10}R^{11}C$-$CR^{10}R^{11}$)—, where $R^{10}$ and $R^{11}$ are identical or different and are each a $C_1$–$C_{20}$-hydrocarbon group, in particular $C_1$–$C_{10}$-alkyl or $C_6$–$C_{14}$-aryl, $R^5$ and $R^{5'}$ are preferably identical or different and are each a $C_6$–$C_{20}$-aryl group which in the para position to the bonding position to the indenyl ring bears a substituent $R^{13}$, $$\text{(ring structure with } R_x, R_y, R^{13}\text{)}$$

where x, y=0, 1 and x+y=0, 1 or 2 and $R^{13}$ is a $C_2$–$C_{10}$alkyl radical, a $C_2$–$C_{10}$-alkenyl radical, a $C_6$–$C_{18}$-aryl radical, a $C_7$–$C_{20}$-arylalkyl radical, a $C_7$–$C_{20}$-alkylaryl radical, a $C_8$–$C_{20}$-arylalkenyl radical, where the hydrocarbon radicals may also be halogenated or partially halogenated by fluorine or chlorine, —$NR_2^{14}$, —$PR_2^{14}$, —$SR^{14}$, —$SiR_3^{14}$, —$NR_3^{14}$ or —$PR_3^{14}$, where $R^{14}$ is as defined for $R^3$.

In formula I, it is very particularly preferred that $M^1$ is zirconium, $R^1$ and $R^2$ are identical and are methyl or chlorine, in particular chlorine, $R^9$ is $R^{10}R^{11}Si=$, $R^{10}R^{11}C=$ or —($R^{10}R^{11}C$-$CR^{10}R^{11}$)—, where $R^{10}$ and $R^{11}$ are identical or different and are hydrogen, phenyl, methyl or ethyl, $R^4$, $R^6$, $R^7$ and $R^8$ and also $R^{4'}$, $R^{6'}$, $R^{7'}$ and $R^{8'}$ are hydrogen, and $R^5$ and $R^{5'}$ are identical or different and are each a $C_6$–$C_{20}$-aryl group, in particular a phenyl, naphthyl or anthracenyl group, which in the para position to the bonding position to the indenyl ring bears a substituent $R^{13}$, where $R^{13}$ is an $SiR_3^{14}$ radical, where $R^{14}$ is as defined for $R^3$ or is a branched $C_3$–$C_{10}$alkyl radical, a $C_2$–$C_{10}$-alkenyl radical or a branched $C_7$–$C_{20}$-alkylaryl radical, where the hydrocarbon radicals may also be halogenated or partially halogenated by fluorine or chlorine.

Preferred metallocene components of the catalyst system of the present invention are combinations of the following molecular fragments of the compound I $M^1R^1R^2$ is $ZrCl_2$, $Zr(CH_3)_2$, $R^3, R^{3'}$ are methyl, ethyl, isopropyl, isobutyl, n-butyl, s-butyl, $R^4, R^8, R^{4'}, R^{8'}$ are hydrogen, $R^6, R^7, R^{6'}, R^{7'}$ are hydrogen, $C_1$–$C_4$-alkyl, $C_6$–$C_{10}$-aryl, $R^5$ and $R^{5'}$ are p-isopropylphenyl, p-tert-butylphenyl, p-s-butyl-phenyl, p-cyclohexyl, p-trimethylsilylphenyl, p-adamantylphenyl, p-$(F_3C)_3$C-phenyl $R^9$ is dimethylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene.

Particularly preferred metallocene compounds of the catalyst system of the present invention are thus the following compounds I dimethylsilanediylbis(2-methyl-4-(p-isopropylphenyl)indenyl)ZrCl$_2$ dimethylsilanediylbis(2-methyl-4-(p-tert-butylphenyl)indenyl)ZrCl$_2$ dimethylsilanediylbis(2-methyl-4-(p-s-butylphenyl)indenyl)ZrCl$_2$ dimethylsilanediylbis(2-methyl-4-(p-cyclohexylphenyl)indenyl)ZrCl$_2$ dimethylsilanediylbis(2-methyl-4-(p-trimethylsilylphenyl)-indenyl)ZrCl2 dimethylsilanediylbis(2-methyl-4-(p-adamantylphenyl)

indenyl)ZrCl$_2$ dimethylsilanediylbis(2-methyl-4-(p-tris (trifluoromethyl)methyl-phenyl)indenyl)ZrCl$_2$ and the corresponding dimethylgermanediyl-, ethylidene-, 1-methylethylidene-, 1,1-dimethylethylidene-, 1,2-dimethyl-ethylidene-, 1,1,2,2-tetramethylethylidene- and dimethylmethylidene-bridged compounds.

Particularly preferred metallecene components are also the corresponding 2-ethyl-, 2-isopropyl-, 2-isobutyl-, 2-n-butyl-, 2-s-butyl-substituted homologues of the abovementioned compounds I. Methods for preparing metallocenes of the formula I are described, for example, in Journal of Organometallic Chem. 288 (1985) 63–67 and in the documents cited therein.

The catalyst system of the present invention preferably further comprises at least one cocatalyst.

The cocatalyst component which may be present according to the present invention in the catalyst system comprises at least one compound of the type of an aluminoxane or a Lewis acid or an ionic compound which reacts with a metallocene to convert the latter into a cationic compound.

As aluminoxane, preference is given to using a compound of the formula II $$(R\ AlO)_n \qquad (II).$$

Aluminoxanes may be, for example, cyclic as in formula III

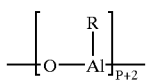  (III)

or linear as in formula IV

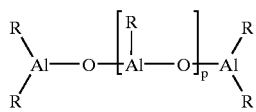  (IV)

or of the cluster type as in formula V, as described in recent literature, cf. JACS 117 (1995), 6465–74, Organometallics 13 (1994), 2957–2969.

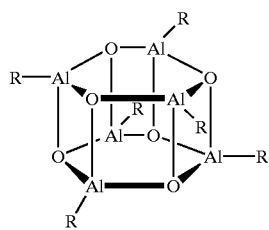  (V)

The radicals R in the formulae (II), (III), (IV) and (V) can be identical or different and are each a C$_1$–C$_{20}$-hydrocarbon group such as a C$_1$–C$_6$-alkyl group, a C6–C$_{18}$-aryl group, benzyl or hydrogen and p is an integer from 2 to 50, preferably from 10 to 35.

Preferably, the radicals R are identical and are methyl, isobutyl, n-butyl, phenyl or benzyl, particularly preferably methyl.

If the radicals R are different, they are preferably methyl and hydrogen, methyl and isobutyl or methyl and n-butyl, with hydrogen, isobutyl or n-butyl preferably being present in a proportion of from 0.01 to 40% (number of radicals R).

The aluminoxane can be prepared in various ways by known methods. One of the methods is to react an aluminum-hydrocarbon compound and/or a hydridoaluminum-hydrocarbon compound with water, which may be gaseous, solid, liquid or bound as water of crystallization, in an inert solvent such as toluene. To prepare an aluminoxane having different alkyl groups R, two different trialkylaluminums (AlR$_3$+AlR'$_3$) corresponding to the desired composition and reactivity are reacted with water, cf. S. Pasynkiewicz, Polyhedron 9 (1990) 429 and EP-A-0 302 424.

Useful metallocenes of the formula I are those which are disclosed in the German Patent Application 197 094 02.3 on page 78, line 21 to page 100, line 22 and in the German Patent Application 197 135 46.3 on page 78, line 14 to page 103, line 22, which are hereby expressly incorporated by reference.

Regardless of the method of preparation, all aluminoxane solutions have in common a variable content of unreacted aluminum starting compound which is present in free form or as adduct.

As Lewis acid, preference is given to using at least one organoboron or organoalumninum compound containing C$_1$–C$_{20}$-groups, such as branched or unbranched alkyl or haloalkyl, eg. methyl, propyl, isopropyl, isobutyl or trifluoromethyl, unsaturated groups such as aryl or haloaryl, eg. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Preferred Lewis acids are trimethylaluminuin, triethylaluminum, truisobutylaluminum, tributylaluminum, trifluoroborane, triphenylborane, tris(4-fluorophenyl) borane, tris(3,5-difluorophenyl)borane, tris(4-fluoromethylphenyl)borane, tris(penta-fluorophenyl)borane, tris(tolyl)borane, tris(3,5-dimethyl-phenyl)borane, tris(3,5-difluorophenyl)borane and/or tris (3,4,5-trifluorophenyl)borane.

Particular preference is given to tris(pentafluorophenyl)borane.

As ionic cocatalysts, preference is given to using compounds which contain a non-coordinating anion such as tetrakis(pentafluorophenyl)borate, tetraphenylborate, SbF$_6^-$, CF$_3$SO$_3^-$ or ClO$_4^-$. Cationic counterions used a re Lewis bases such as methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene and triphenylcarbeniuyo.

Ionic compounds which can be used according to the present invention are triethylammonium tetra(phenyl) borate, tributylammonium tetra(phenyl)borate, trimethylammonium tetra(tolyl)borate, tributylammonium tetra(tolyl) borate, tributylammonium tetra(pentafluorophenyl)borate, tributylammonium tetrak(spentaffluorophenyl) a luminate, tripropylammonium tetra(dimet hylphenyl)bborate, tributylammonium tetra(trifluoromethylphenyl )borate, tributylammonium tetra(4-fluorophenyl)borate, N,N-dimethylanilinium tetral(phenyld)borate, N,N-diethylanilinium tetra(phenyl)borate, N,N-dimethylanilinium tetrakis(pentafluorophenyl)borate, N,N-dimethylanilinium tetrakis(pentafluorophenyl)aluminate, di(propyl)ammonium tetrakis(pentafluorophenyl)borate, di(cyclohexyl)ammonium tetrakist(pentafluorophenyl) borate, triphenylphosphonium tetrakis(phenyl)borate, triethylphosphonium tetrakis(phenyl)borate, diphenylphosphonium tetrakis(phenyl)borate, tri(methylphenyl) phosphonium tetrakis (phenyl)borate, tri(dimethylphenyl) phosphonium tetrakis(phenyl)borate, triphenylcarbenium tetrakis(pentafluorophenyl)borate, triphenylcarbenium tetrakis(pentafluorophenyl) aluminate, triphenylcarbenium tetrakis(phenyl)aluminate, ferrocenium tetrakis (pentafluorophenyl)borate and/or ferrocenium tetrakis (pentafluorophenyl)aluminate.

Preference is given to triphenylcarbenium tetrakis (pentafluorophenyl)borate and/or N,N-dimethylanilinium tetrakis(pentafluorophenyl)borate.

It is also possible to use mixtures of at least one Lewis acid and at least one ionic compound.

Other useful cocatalyst components are likewise borane or carborane compounds such as 7,8-dicarbaundecaborane (13), undecahydrido-7,8-dimethyl-7,8-dicarbaundecaborane, dodecahydrido-1-phenyl-1,3-dicarbanonaborane, tri(butyl)ammoniumun decahydrido-8-ethyl-7,9-dicarbaundecaborate, 4-carbanonaborane(14), bis (tri(butyl)ammonium)nonaborate, bis(tri(butyl)ammonium) undecaborate, bis(tri(butyl)ammonium)dodecaborate, bis(tri (butyl)ammonium)decachlorodecaborate, tri(butyl) ammonium 1-carbadecaborate, tri(butyl)ammonium 1-carbadodecaborate, tri(butyl)ammonium 1-trimethylsilyl-1-carbadecaborate, tri(buyl)ammonium bis(nonahydrido-1, 3-dicarbanonaborato)cobaltate(III), tri(butyl)ammonium bis (undecahydrido-7,8-dicarbaundecaborato)ferrate(III).

The support component of the catalyst system of the present invention can be any organic or inorganic, inert solid, in particular a porous support such as talc, inorganic oxides and finely divided polymer powders, polyolefins.

Suitable inorganic oxides are found in Groups 2, 3, 4, 5, 13, 14, 15 and 16 of the Periodic Table of the Elements. Preferred oxides for supports are silicon dioxide, aluminum oxide and also mixed oxides of the two elements and the corresponding oxide mixtures. Other inorganic oxides which can be used alone or in combination with the preferred oxidic supports mentioned are MgO, $ZrO_2$, $TiO_2$ or $B_2O_3$.

The support materials used have a specific surface area in the range from 10 to 1000 $m^2/g$, a pore volume in the range from 0.1 to 5 ml/g and a mean particle size of from 1 to 500 $\mu$m. Preference is given to supports having a specific surface area in the range from 50 to 500 $\mu$m, a pore volume in the range from 0.5 to 3.5 ml/g and a mean particle size in the range from 5 to 350 $\mu$m. Particular preference is given to supports having a specific surface area in the range from 200 to 400 $m^2/g$, a pore volume in the range from 0.8 to 3.0 ml/g and a mean particle size of from 10 to 200 $\mu$m.

If the support material used naturally has a low moisture content or residual solvent content, dehydration or drying before use can be omitted. If this is not the case, as when using silica gel as support material, dehydration or drying is advisable. Thermal dehydration or drying of the support material can be carried out under reduced pressure with simultaneous inert gas blanketing (nitrogen). The drying temperature is in the range from 100° C. to 1000° C., preferably from 200° C. to 800° C. The pressure is not critical in this case. The duration of the drying process can be from 1 to 24 hours. Shorter or longer drying times are possible, provided that equilibrium with the hydroxyl groups on the support surface can be established under the conditions selected which normally takes from 4 to 8 hours.

Dehydration or drying of the support material can also be carried out by chemical means, by reacting the adsorbed water and the hydroxyl groups on the surface with suitable passivating agents. Reaction with the passivating reagent can convert the hydroxyl groups completely or partially into a form which leads to no adverse interaction with the catalytically active centers. Suitable passivating agents are silicon halides and silanes, eg. silicon tetrachloride, chlorotrimethylsilane or dimethylaminotrichlorosilane, or organometallic compounds of aluminum, boron and magnesium, eg. trimethylaluminum, triethylaluminum, triisobutylaluminum, triethylborane or dibutylmagnesium. The chemical dehydration or passivation of the support material is carried out by reacting, with-exclusion of air and moisture, a suspension of the support material in a suitable solvent with the passivating reagent in pure form or dissolved in a suitable solvent. Suitable solvents are aliphatic or aromatic hydrocarbons such as pentane, hexane, heptane, toluene or xylene. The passivation is carried out at from 25° C. to 120° C., preferably from 50° C. to 70° C. Higher and lower temperatures are possible. The duration of the reaction is from 30 minutes to 20 hours, preferably from 1 to 5 hours. After the chemical dehydration is complete, the support material is isolated by filtration under inert conditions, washed one or more times with suitable inert solvents as described above and subsequently dried in a stream of inert gas or under reduced pressure.

Organic support materials such as finely divided polyolefin powders, eg. polyethylene, polypropylene or polystyrene, can also be used and should, before use, likewise be freed of adhering moisture, solvent residues or other impurities by means of appropriate purification and drying operations.

To prepare the supported catalyst system, at least one of the above-described metallocene components is brought into contact in a suitable solvent with at least one cocatalyst component, preferably giving a soluble reaction product, an adduct or a mixture.

The composition obtained in this way is then mixed with the dehydrated or passivated support material, the solvent is removed and the resulting supported metallocene catalyst system is dried to ensure that the solvent is completely or mostly removed from the pores of the support material. The supported catalyst is obtained as a free-flowing powder.

A process for preparing a free-flowing and, if desired, prepolymerized supported catalyst system comprises the following steps:

a) preparing a metallocene/cocatalyst mixture in a suitable solvent or suspension medium, where the metallocene component has one of the above-described structures, b) applying the metallocene/cocatalyst mixture to a porous, preferably inorganic, dehydrated support, c) removing the major part of solvent from the resulting mixture, d) isolating the supported catalyst system and e) if desired, prepolymerizing the resulting supported catalyst system with one or more olefinic monomer(s) to obtain a prepolymerized supported catalyst system.

Preferred solvents for the preparation of the metallocene/ cocatalyst mixture are hydrocarbons and hydrocarbon mixtures which are liquid at the reaction temperature selected and in which the individual components preferably dissolve. The solubility of the individual components is, however, not a prerequisite as long as it is ensured that the reaction product of metallocene and cocatalyst components is soluble in the solvent selected. Suitable solvents are alkanes such as pentane, isopentane, hexane, heptane, octane and nonane, cycloalkanes such as cyclopentane and cyclohexane and aromatics such as benzene, toluene, ethylbenzene and diethylbenzene. Very particular preference is given to toluene.

The amounts of aluminoxane and metallocene used in the preparation of the supported catalyst system can be varied within a wide range. Preference is given to using a molar ratio of aluminum to transition metal in the metallocene of from 10:1 to 1000:1, very particularly preferably from 50:1 to 500:1. In the case of methylaluminoxane, preference is given to using 30% strength toluene solutions, but the use of 10% strength solutions is also possible.

For the preactivation, the metallocene in the form of a solid is dissolved in a solution of the aluminoxane in a suitable solvent. It is also possible to dissolve the metallocene separately in a suitable solid and subsequently to combine this solution with the aluminoxane solution. Preference is given to using toluene. The preactivation time is from 1 minute to 200 hours. The preactivation can take place at room temperature of 25° C. The use of higher temperatures can in individual cases reduce the preactivation time required and give an additional increase in activity. Elevated temperatures in this case refer to a range from 50° C. to 100° C.

The preactivated solution or the metallocene/cocatalyst mixture is subsequently combined with an inert support material, usually silica gel, which is in the form of a dry powder or as a suspension in one of the abovementioned solvents. The support material is preferably used as powder. The order of addition is unimportant. The preactivated metallocene/cocatalyst solution or the metallocene/cocatalyst mixture can be added to the initially charged support material, or else the support material can be introduced into the initially charged solution.

The volume of the preactivated solution or the metallocene/cocatalyst mixture can exceed 100% of the total pore volume of the support material used or else be up to 100% of the total pore volume.

The temperature at which the preactivated solution or the metallocene/cocatalyst mixture is brought into contact with the support material can vary within the range from 0° C. to 100° C. Lower or high temperatures are, however, also possible.

Subsequently, the solvent is completely or mostly removed from the supported catalyst system; during this procedure, the mixture can be stirred and, if desired, also heated. Preferably, both the visible proportion of the solvent and the proportion in the pores of the support material are removed. The removal of the solvent can be carried out in a conventional way using reduced pressure and/or purging with inert gas. During the drying process, the mixture can be heated until the free solvent has been removed, which usually takes from 1 to 3 hours at a preferred temperature of from 30° C. to 60° C. The free solvent is the visible proportion of solvent in the mixture. For the purposes of the present invention, residual solvent is the proportion present in the pores.

As an alternative to complete removal of the solvent, the supported catalyst system can also be dried only as far as a particular residual solvent content, with the free solvent having been completely removed. Subsequently, the supported catalyst system can be washed with a low-boiling hydrocarbon such as pentane or hexane and dried again.

The supported catalyst system prepared according to the present invention can be used either directly for the polymerization of olefins or be prepolymerized with one or more olefinic monomers prior to use in a polymerization process. The procedure for the prepolymerization of supported catalyst systems is described in WO 94/28034.

As additive, it is possible to add, during or after the preparation of the supported catalyst system, a small amount of an olefin, preferably an α-olefin such as styrene or phenyl-dimethylvinylsilane as activity-increasing component or an antistatic, as described in U.S. Ser. No. 08/365,280. The molar ratio of additive to metallocene component compound I is preferably from 1:1000 to 1000:1, very particularly preferably from 1:20 to 20:1.

The present invention also provides a process for preparing a polyolefin by polymerization of one or more olefins in the presence of the catalyst system of the present invention comprising at least one transition metal component of the formula I. For the purposes of the present invention, the term polymerization refers to both homopolymerization and copolymerization.

Preference is given to polymerizing olefins of the formula $R_m$—CH=CH—$R_n$, where $R_m$ and $R_n$ are identical or different and are each a hydrogen atom or a radical having from 1 to 20 carbon atoms, in particular from 1 to 10 carbon atoms, and $R_m$ and $R_n$ together with the atoms connecting them can form one or more rings.

Suitable olefins are 1-olefins having from 2 to 40, preferably from 2 to 10, carbon atoms, eg. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the present invention, preference is given to homopolymerizing propene or ethene or copolymerizing propene with ethene and/or one or more 1-olefins having from 4 to 20 carbon atoms, eg. hexene, and/or one or more dienes having from 4 to 20 carbon atoms, eg. 1,4-butadiene, norbornadiene, ethylidenenorbornene or ethylnorbornadiene. Suitable copolymers are ethene-propene copolymers or ethene-propene-1,4-hexadiene terpolymers.

The polymerization is carried out at from −60° C. to 300° C., preferably from 50° C. to 200° C., very particularly preferably from 50° C. to 80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the present invention can be used as sole catalyst component for the polymerization of olefins having from 2 to 20 carbon atoms, or preferably in combination with at least one alkyl compound of elements of Main Groups I to III of the Periodic Table, for example an aluminum alkyl, magnesium alkyl or lithium alkyl or an aluminoxane. The alkyl compound is added to the monomer or suspension medium and serves to free the monomer of substances which can impair the catalytic activity. The amount of alkyl compound added depends on the quality of the monomers used.

As molar mass regulator and/or to increase the activity, hydrogen is added if required.

In the polymerization, it is also possible to meter an antistatic into the polymerization system, either together with or separately from the catalyst system used.

The polymers prepared using the catalyst system of the present invention display a uniform particle morphology and contain no fines. No deposits or caked material are obtained in the polymerization using the catalyst system of the present invention.

The catalyst system of the present invention gives polymers such as polypropylene having extraordinarily high stereospecificity and regiospecificity.

Particularly characteristic for the stereospecificity and regiospecificity of polymers, in particular polypropylene, is the triad tacticity (TT) and the proportion of 2-1-inserted propene units (RI), which can be determined from the $^{13}$C NMR spectra.

The $^{13}$C NMR spectra are measured in a mixture of hexachlorobutadiene and d$_2$-tetrachloroethane at elevated temperature, eg. 365 K. All $^{13}$C NMR spectra of the polypropylene samples measured are calibrated on the basis of the resonance signal of d$_2$-tetrachloro-ethane ($\delta$=73.81 ppm).

The triad tacticity of the polypropylene is determined from the methyl resonance signals in the $^{13}$C NMR spectrum from 23 to 16 ppm, cf. J. C. Randall, Polymer Sequence Determination: Carbon 13 NMR Method, Academic Press New York 1978, A. Zambelli, P. Locatelli, G. Bajo, F. A. Bovey, Macromolucules 8 (1975), 687–689, H. N. Cheng, J. A. Ewen, Makromol. Chem. 190 (1989), 1931–1943. Three successive 1-2-inserted propene units whose methyl groups are arranged on the same side in the "Fischer projection" are referred to as mm triads ($\delta$=21.0 ppm to 22.0 ppm). If only the second methyl group of the three successive propene units points to the other side, the sequence is referred to as an rr triad ($\delta$=19.5 ppm to 20.3 ppm) and if only the third methyl group of the three successive propene units points to the other side, the sequence is referred to as an mr triad ($\delta$=20.3 ppm to 21.0 ppm). The triad tacticity is calculated according to the following formula TT (%)=mm/(mm+mr+rr)×100

If a propene unit is inserted in reverse into the growing polymer chain, this is referred to as a 2 1 insertion, cf. T. Tsutsui, N. Ishimaru, A. Mizuno, A. Toyota, N. Kashiwa, Polymer 30, (1989), 1350–56. The following different structural arrangements are possible:

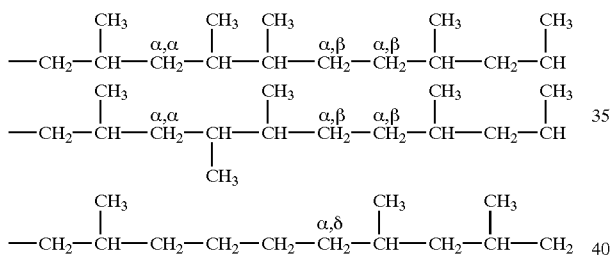

The proportion of 2-1-inserted propene units (RI) can be calculated according to the following formula:

RI (%) 0.5 Ia,β(Ia,a+Ia,β+Ia,d)×100, where

Ia,a is the sum of the intensities of the resonance signals at $\delta$=41.84, 42.92 und 46.22 ppm, Ia,β is the sum of the intensities of the resonance signals at β=30.13, 32.12, 35.11 and 35.57 ppm and Ia,d is the intensity of the resonance signal at $\delta$=37.08 ppm.

A particularly high regiospecificity also gives a particularly high melting point of the polymer, in particular the isotactic polypropylene. The isotactic polypropylene which has been prepared using the catalyst system of the present invention has a proportion of 2-1-inserted propene units RI<0.5% at a triad tacticity TT>98.0% and a melting point >156° C., and the M$_w$/M$_n$ of the polypropylene prepared according to the present invention is from 2.5 to 3.5.

The copolymers which can be prepared using the catalyst system of the present invention have a significantly higher molar mass compared to the prior art. At the same time, such copolymers can be prepared using the catalyst system of the present invention at a high productivity and at industrially relevant process parameters without deposit formation.

The polymers prepared by the process of the present invention are suitable, in particular, for producing strong, hard and stiff shaped products such as fibers, filaments, injection-molded parts, films, sheets or large hollow bodies such as pipes.

EXAMPLES

General Procedures

The preparation and handling of the organometallic compounds was carried out with exclusion of air and moisture under argon using the Schlenk technique or in a glove box. All solvents required were purged with argon and dried over molecular sieves before use.

The metallocenes used were characterized using $^1$H-NMR, $^{13}$C-NMR and IR spectroscopy.

Abbreviations

PP=polypropylene

MC=metallocene cat=supported catalyst system h=hour

VN=viscosity number in cm$^3$/g

M$_w$=weight average molar mass in g/mol

M$_w$/M$_n$=polydispersity, determined by gel permeation chromatography

BD=bulk density in g/dm$^3$ and m.p.=melting point in ° C., determined by differential scanning calorimetry (DSC)

TT=triad tacticity in percent determined by $^{13}$C-NMR spectroscopy

RI=reverse insertions in %, determined by $^{13}$C-NMR spectroscopy

Tg=glass transition temperature in ° C., determined by differential scanning calorimetry Example 1

Preparation of the Supported Catalyst System 67 mg (0.091 mmol) of rac-dimethylsilanediylbis(2-methyl-4-(para-tert-butylphenyl)indenyl)zirconium dichloride were dissolved at room temperature in 4.3 cm$^3$ (20 mmol of Al) of 30% strength methylaluminoxane solution in toluene. The solution was diluted with 3.7 cm$^3$ of toluene and stirred in the dark at 25° C. for 1 hour. This solution was added a little at a time while stirring to 4 g of SiO$_2$²) and, after addition was complete, the mixture was stirred further for 10 minutes. The ratio of volume of solution to total pore volume of the support material was 1.25. The mixture was subsequently dried at 40° C. and 10$^{-3}$ mbar for 4 h. This gave 5.6 g of a free-flowing, gray-brown powder which, according to elemental analysis, contained 0.16% by weight of Zr and 9.5% by weight of Al.

Polymerization

A dry 16 dm$^3$ reactor which had been flushed first with nitrogen and subsequently with propene was charged with 10 dm$^3$ of liquid propene. 8 cm$^3$ of 20% strength triethylaluminum solution in Varsol® from Witco were added as scavenger and the mixture was stirred at 30° C. for 15 minutes. Subsequently, a suspension of 2 g of the supported metallocene catalyst in 20 cm$^3$ of Exxsol was introduced into the reactor, the mixture was heated to the polymerization temperature of 65° C. and the polymerization system was held at 65° C. for 1 hour. The polymerization was stopped by venting and the polymer obtained was dried under reduced pressure. This gave 3.2 kg of polypropylene powder.

The catalyst activity was 134kg of PP/(g of MC×h) or 1.6 kg of PP/(g of cat×h)

The isotactic polypropylene prepared had the following properties:

M.p. 159° C., $M_w$=900,000 g/mol, $M_w/M_n$=2.6, VN=760 cm$^3$/g,

BD=460 g/dm$^3$, TT=98.9%, RI=0.36%.

1) Albemarle Corporation, Baton Rouge, La., USA 2) Silica Typ MS 948, W.R. Grace, Davison Chemical Division, Baltimore, Md., USA, pore volume 1.6 ml/g, calcined at 600° C.

Comparative Example 1

Preparation of the Supported Catalyst System

The preparation was carried out using a method similar to Example 1, but using 58 mng (0.091 mnmol) of rac-dimethylsilane-diylbis (2-methyl-4-phenylindenyl) zirconium dichioride as metallocene component. This gave 5.8 g of a free-flowing, pink powder which, according to elemental analysis, contained 0.15% by weight of Zr and 9.7% by weight of Al.

Polymerization

The polymerization was carried out using a method similar to Example 1. This gave 2.3 kg of polypropylene powder.

The catalyst activity was 115 kg of PP/(g of MC×h) or 1.15 kg of PP/(g of cat×h).

The isotactic polypropylene prepared had the following properties:

M.p.=149° C., $M_w$=850,000 g/mol, $M_w/M_n$=2.7, VN=710 cm$^3$/g,

BD=420 g/dm$^3$, TT=98.3%, RI=0.8%.

Example 2

The polymerization was carried out using a method similar to Example 1, but 5 standard Ndm$^3$ of hydrogen were additionally used in the polymerization and the polymerization time was 30 minutes. This gave 2.9 kg of polypropylene powder.

The catalyst activity was 242 kg of PP/(g of MC×h) or 2.9 kg of PP/(g of cat×h).

The isotactic polypropylene prepared had the following properties:

M.p.=160° C., $M_w$=450,000 g/mol, $M_w/M_n$=3.2, VN=370 cm$^3$/g,

BD=450 g/dm$^3$, TT=98.9%, RI=0.3%.

Examples 3 and 4

A dry 24 dm$^3$ reactor was flushed with propylene and charged with 12 dm$^3$ of liquid propylene, 150 g of ethylene (Example 3) or 450 g of ethylene (Example 4) and 22 cm$^3$ of a triisobutylaluminum solution in hexane (8 mmol of Al, 2 cm$^3$ of triisobutylaluminum diluted with 20 cm$^3$ of hexane) and the reactor stirring was set to 250 rpm. 0.7 g of the supported catalyst prepared in Example 1 was suspended in 25 cm$^3$ of a dearomitized petroleum fraction having a boiling range of from 100° C. to 120° C. and the suspension was introduced into the reactor. The reactor was heated to the polymerization temperature of 70° C. (7.5° C./min) and held at this polymerization temperature for 1 hour by cooling the reactor jacket. The polymerization was stopped by quickly venting the excess momonmers. The polymer was dried under reduced pressure. Polymer yield, catalyst activity and product data are shown in Table 1.

Comparative Examples 2 and 3

The procedure of Examples 3 and 4 was repeated, but the catalyst used was the supported catalyst from Comparative Example 1. The results are shown in Table 1. When using the catalyst system which is not according to the present invention, the molar mass $M_w$ is significantly lower than in Examples 3 and 4 in which the catalyst system of the present invention was used.

Comparative Examples 4 and 5

Using a method similar to Comparative Example 1, a supported catalyst was prepared using rac-dimethylsilanediylbis(2-methyl-4-naphthyl-1-indenyl) zirconium dichloride as metallocene component.

The polymerization using this supported catalyst was carried out using a method similar to Comparative Examples 2 and 3. The results are shown in Table 1.

Example 5

A dry 24 dm$^3$ reactor was flushed with propylene and 0.5 bar of hydrogen was introduced. The reactor was subsequently charged with 12 dm$^3$ of liquid propylene and 22 cm$^3$ of a triisobutylaluminum solution in hexane (8 mmol of Al, 2 cm$^3$ of triisobutylaluminum diluted with 20 cm$^3$ of hexane) and the reactor stirring was set to 250 rpm. 0.7 g of the supported catalyst prepared in Example 1 was suspended in 25 cm$^3$ of a dearomitized petroleum fraction having a boiling range of from 100° C. to 120° C. and the suspension was introduced into the reactor. The reactor was heated to the polymerization temperature of 701° C. (7.5° C./min) and held at this polymerization temperature for 1 hour by cooling the reactor jacket.

The reactor was subsequently depressurized to 10 bar and 20 bar of ethylene were introduced. The mixture was polymerized further at 60° C. for 2 hours and the polymerization was then stopped by rapid venting of the excess monomers.

This gave a block copolymer having the following properties:

Homopolymer matrix (iPP from fractionation)

M.p.=157° C., $M_w$=280,000 g/mol, $M_w/M_n$=2.6, VN=230 cm$^3$/g, rubber (ethylene-propylene copolymer)

$T_g$=49° C., 44% by weight of $C_2$, VN 374 cm$^3$/g, $M_w$=402,500 g/mol, $M_w/M_n$=3.0.

Comparative Example 6

Example 5 was repeated using a supported catalyst prepared as described in Comparative Example 1.

This gave a block copolymer having the following properties:

Homopolymer matrix (iPP from fractionation)

M.p.=152° C., $M_w$=167,500 g/mol, $M_w/M_n$=2.7, VN=147 cm$^3$/g, rubber (ethylene-propylene copolymer)

$T_g$=−48 ° C. 42% by weight Of $C_2$, VN=182 cm$^3$/g, $M_w$=224,000 g/mol, $M_w/M_n$=2.9.

Comparative Example 7

Example 5 was repeated using a supported catalyst prepared as described in Comparative Example 4.

This gave a block copolymer having the following properties:

Homopolymer matrix (iPP from fractionation)

M.p.=154° C., $M_w$=198,500 g/mol, $M_w/M_n$=2.6, VN=168 cm$^3$/g, rubber (ethylene propylene copolymer)

$T_g$=–50° C., 46% by weight of $C_2$, VN=280 cm$^3$/g, $M_w$=354,000 g/mol, $M_w/M_n$=2,7.

| Ex. | Yield [kg PP] | Activity [kg PP/g/h] | M.p. [° C.] | VN [cm$^3$/g] | $M_w$ [g/mol] | $M_w/M_n$ | $C_2$ content [% by wt.] |
|---|---|---|---|---|---|---|---|
| 3 | 2.24 | 3.2 | 140 | 628 | 815000 | 2.2 | 3.0 |
| 4 | 2.38 | 3.4 | 109 | 436 | 586000 | 2.4 | 10.6 |
| C2 | 1.47 | 2.1 | 135 | 248 | 295500 | 2.3 | 3.1 |
| C3 | 1.61 | 2.3 | 105 | 198 | 214000 | 2.3 | 10.5 |
| C4 | 1.19 | 1.7 | 133 | 489 | 508500 | 2.3 | 3.0 |
| C5 | 1.26 | 1.8 | 106 | 401 | 464000 | 2.8 | 10.5 |

We claim:

1. A supported catalyst system comprising at least one metallocene component comprising at least one compound of the formula I below

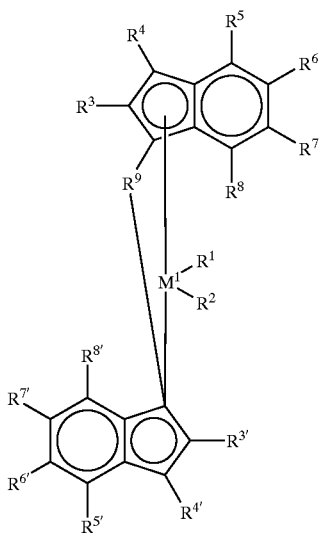

(I)

where
- $M^1$ is a metal of Group IVb of the Periodic Table of the Elements,
- $R^1$ and $R^2$ are identical or different and are each a hydrogen atom, a $C_{1-C10}$-alkyl group, a $C_1$–$C_{10}$-alkoxy group, a $C_6$–$C_{20}$-aryl group, a $C_6$–$C_{10}$-aryloxy group, a $C_2$–$C_{10}$-alkeny group, an OH group, an $NR^{12}_2$ group, where $R^{12}$ is a $C_1$–$C_{10}$-alkyl group or $C_6$–$C_{14}$-aryl group, or a halogen atom,
- $R^3$, $R^4$, $R^6$, $R^7$, $R^8$ and also $R^{3'}$, $R^{4'}$, $R^{6'}$, $R^{7'}$, $R^{8'}$ are identical are identical or different and are each a hydrogen atom, an unsubstituted or halogenated, linear, cyclic or branched, $C_1$–$C_{10}$-alkyl group, $C_2$–$C_{10}$-alkenyl group, $C_6$–$C_{20}$-aryl group, $C_7$–$C_{40}$-arylalkyl group, $C_7$–$C_{40}$-alkylaryl group or $C_8$–$C_{40}$-arylalkenyl group, with the proviso that $R^3$ and $R^{3'}$ are not hydrogen, and
- $R^5$ and $R^{5'}$ are identical or different and are each a $C_6$–$C_{40}$-aryl group of the formula

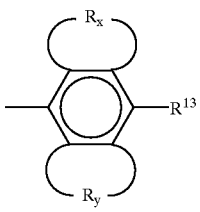

where x, y=0, 1 and x+y=0, 1 or 2, where the aromatic ring system x and/or the aromatic ring system y can also be linked to the radicals $R^6$, $R^{6'}$ or $R^4$, $R^{4'}$, and where the $C_6$–$C_{40}$-aryl group bears a substituent $R^{13}$ in the para position to the bonding position on the indenyl ring, and $R^{13}$ is a tert-butyl, p-adamantyl or $(F_3C)_3C$, $R^9$ is a bridge

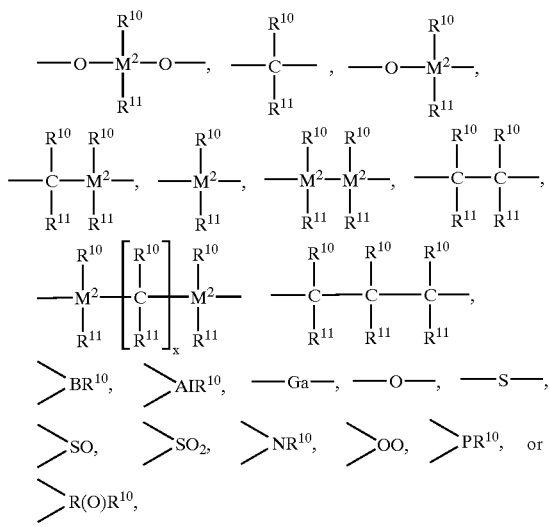

where $R^{10}$ and $R^{11}$, even when bearing the same index, can be identical or different and are each a hydrogen atom, a halogen atom or a $C_{1-C20}$-alkyl group, a $C_{1-C10}$-fluoroalkyl group, a $C_1$–$C_{group,\ a\ C6}$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C8$–$C_{40}$-arylalkenyl group, or $R^{10}$ and $R^{11}$ together with the atoms connecting them form one or more rings, z is an integer from zero to 18 and $M^2$ is silicon, germanium or tin, and at least one cocatalyst and at least one support.

2. A catalyst system as claimed in claim 1 comprising at least one metallocene component comprising at least one compound of the formula 1, wherein $M^1$ is zirconium, hafnium or titanium, $R^1$ and $R^2$ are identical and are methyl or chlorine, $R^3$ and $R^{3'}$ are identical or different and are each an unsubstituted or halogenated, linear, cyclic or branched, $C_1$–$C_{10}$-alkyl group, $C_2$–$C_{10}$-alkenyl group or $C_7$–$C_{40}$-alkylaryl group, $R^9$ is $R^{10}R^{11}Si=$, $R^{10}R^{11}Ge=$, $R^{10R11}C=$ or $-(R^{10}R^{11}-C-C\ R^{10}R^{11})-$, where $R^{10\ and\ R11}$ are identical or different and are each a $C_{1-C10}$-alkyl or $C_6$–$C_{14}$-aryl group.

3. A catalyst system as claimed in claim 1 comprising at least one metallocene component comprising at least one compound of the formula 1, wherein $M^1$ is zirconium, $R^1$ and $R^2$ are identical and are methyl or chlorine, $R^9$ is $R^{10}R^{11}Si=$, $R^{10}R^{11}C=$ or $-(R^{10}R^{11}\text{-C-C}R^{10}R^{11})-$, where $R^{10}$ and $R^{11}$ are identical or different and are hydrogen, phenyl, methyl or ethyl, $R^4$, $R^6$, $R^7$ and $R^8$ and also $R^{4\prime}$, $R^{6\prime}$, $R^{7\prime}$ and $R^{8\prime}$ are hydrogen.

4. A catalyst system as claimed in claim 1 comprising at least one metallocene component comprising at least one compound of the formula 1, wherein $M^1R^1R^2$ is $ZrCl_2$, $Zr(CH_3)_2$, $R^3$, $R^{3\prime}$ are methyl, ethyl, isopropyl, isobutyl, n-butyl, s-butyl, $R^4$ $R^8$, $R^{4\prime}$, $R^{8\prime}$ are hydrogen, $R^6$, $R^7$, $R^{6\prime}$, $R^{7\prime}$ are hydrogen, $C_1$–$C_4$-alkyl, $C_6$–$C_{10}$-aryl, $R^5$ and $R^{5\prime}$ are p-tert-butylphenyl, p-adamantylphenyl or p-$(F_3C)_3$C-phenyl, $R^9$ is dimethylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene.

5. A process for preparing a supported catalyst system as claimed in claim 1 as a free flowing powder, wherein a) a metallocene/cocatalyst mixture in a suitable solvent or suspension medium is prepared, b) the metallocene/cocatalyst mixture is applied to a porous, inorganic, dehydrated support, c) the solvent is removed from the resulting mixture and d) the supported catalyst system is isolated.

6. A process for preparing a free-flowing supported catalyst system as claimed in claim 5, wherein e) the supported catalyst system obtained is prepolymerized with one or more olefinic monomers.

7. A free-flowing supported catalyst system obtained by the process as claimed in claim 5.

8. A process for producing a homopolymer and/or copolymer of monomers having the formula $R_m$—CH═CH—$R_n$, where $R_m$ and $R_n$ are identical or different and are each a hydrogen atom or a group having from 1 to 20 carbon atoms, and $R_m$ and $R_n$ together with the atoms connecting them can form one or more rings by polymerizing said monomers in the presence of a supported catalyst system claimed in claim 2.

9. A process for preparing a homopolymer and/or copolymer as claimed in claim 8 which is carried out in solution, in bulk, in suspension or in the gas phase, continuously or batchwise, in one or more stages.

10. A polymer produced by the process as claimed in claim 8.

11. Fibers, filaments, injection-molded parts, films, sheets and large hollow bodies produced from the polymer as claimed in claim 10.

* * * * *

UNITED STATES PATENT AND TRADEMARK OFFICE
CERTIFICATE OF CORRECTION

PATENT NO. : 6,444,606 B1
DATED : September 3, 2002
INVENTOR(S) : Bingel et al.

It is certified that error appears in the above-identified patent and that said Letters Patent is hereby corrected as shown below:

Column 15,
Line 57, "$C_{1-C10}$-alkyl" should be -- $C_1$-$C_{10}$-alkyl --.

Column 16,
Line 47, "$C_{1-C20}$-alkyl" should be -- $C_1$-$C_{20}$-alkyl --.
Line 48, "$C_{1-C10}$-fluoroalkyl" should be -- $C_1$-$C_{10}$-fluoroalkyl --;
"$C_1$-$C_{Igroup,\ a\ C6}$-$C_{10}$-" should be -- $C_1$-$C_{10}$-alkoxy group, a $C_6$-$C_{14}$-aryl group, a $C_6$-$C_{10}$- --.
Line 51, "$C8$-$C_{40}$-" should be -- $C_8$-$C_{40}$- --.
Line 66, "$R^{10R11}C=$" should be -- $R^{10}R^{11}C=$ --.
Line 67, "$and\ R11$" should be -- and $R^{11}$ --.

Column 17,
Line 1, "$C_{1-C10}$-alkyl" should be -- $C_1$-$C_{10}$-alkyl --.
Line 20, "$R^4\ R^8$," should be -- $R^4, R^8,$ --.

Signed and Sealed this

Twenty-eighth Day of January, 2003

JAMES E. ROGAN
*Director of the United States Patent and Trademark Office*